United States Patent [19]

McKibben

[11] 3,954,968

[45] May 4, 1976

[54] COMPOSITION FOR ATTRACTING THE COTTON BOLL WEEVIL

[75] Inventor: Gerald H. McKibben, Starkville, Miss.

[73] Assignee: The United States of America as represented by the Secretary of Agriculture, Washington, D.C.

[22] Filed: Feb. 27, 1975

[21] Appl. No.: 554,056

[52] U.S. Cl.................................. 424/84; 424/357
[51] Int. Cl.².......................................... A01N 17/14
[58] Field of Search....................................... 424/84

[56] References Cited
UNITED STATES PATENTS
3,803,303    4/1974    McKibben et al................... 424/84

OTHER PUBLICATIONS
J. Econ. Entomol. Vol. 64, pp. 317–319, (1971).
J. Econ. Entomol. Vol. 65, pp. 97–100, (1972).
J. Econ. Entomol., Vol. 66, pp. 566–567, (Apr. 1973).
J. Econ. Entomol., Vol. 52, pp. 1138–1143, (1959).

*Primary Examiner*—Donald B. Moyer
*Attorney, Agent, or Firm*—M. Howard Silverstein; Salvador J. Cangemi

[57] ABSTRACT

A synthetically prepared boll weevil attractant has been formulated so as to include crude cottonseed oil. This formulation, in the form of a gelled emulsion, has been used to trap and destroy boll weevils for periods up to 2 weeks. The new formulation releases the active ingredients at a more favorable rate and is effective for longer periods than previously developed ones.

1 Claim, No Drawings

COMPOSITION FOR ATTRACTING THE COTTON BOLL WEEVIL

This invention relates to insect-controlling formulations. More specifically this invention relates to insect-control formulations which contain a synthetically prepared boll weevil attractant and crude cottonseed oil to yield effective preparations yielding a sustained release of the active ingredients.

The main object of this invention is to provide a species-specific control method that will not affect non-target insect species or higher animals.

Another object of the invention is to provide a process whereby synthetic and natural attractants and aggregants can be formulated so as to have prolonged activity in the field and provide an inexpensive survey and control technique.

The invention described herein has been shown to attract cotton boll weevils (*Anthonomus granois*) and to provide a long enough residual activity to prove economically feasible.

BACKGROUND AND PRIOR ART

Sex pheromones (attractants) of several different insects have been synthesized and investigative work by these inventors is being continued with others. Each of the synthetic materials possesses potential as a control agent and/or survey tool when formulated in a manner as to render them suitable for field use.

The boll weevil sex pheromone synthesis was reported by J. H. Tumlinson in Science, pp. 1010-2 (1969) in a paper bearing the title, "Sex Pheromones Produced by Male Boll Weevil: Isolation, Identification, and Synthesis." It has been noted that the synthetic pheromone, while a potent attractant, possesses a very short residual life span. When deposited on firebrick or other absorptive materials, it is active for periods only up to about 24 hours under field conditions. G. H. McKibben, et al. used various polymers, resins, and waxes to formulate this attractant into compressed tablets which gave a slow, sustained release of the attractant over long periods of time. These preliminary studies were reported in "Slow Release of Grandlure, the Synthetic Pheromone of the Boll Weevil," which was published in the Journal of Economic Entomology, Vol. 64, pp. 317-19, 1970. A later improvement was reported by Hardee et al. (J. Econ. Entomol., Vol. 65, pp. 97-100, 1972) wherein the grandlure was incorporated into a solution of polyethylene glycol, methanol, glycerol, and water and absorbed onto cigarette filters. This formulation was effective in attracting boll weevils to traps for periods of 1 week or less.

THE PRESENT INVENTION

Subsequent research by the authors has yielded a formulation that is effective in attracting boll weevils for periods of up to 2 weeks. Specifically, the invention involves mixing the attractant with a crude cottonseed oil emulsion. The formulation is aided by the cottonseed oil in regulating the release of the grandlure and possibly in offering other attractants present in the crude cottonseed oil.

The actual preparation can be carried out with variations, and the following examples are provided to illustrate certain preferred embodiments. These examples should not be construed as limitations in any manner whatever.

SUMMARY

The present invention can best be described as an improved effective composition for attracting the boll weevil, *Anthonomus grandis* Boheman, the improvement comprising incorporating a synthetic boll weevil attractant (grandlure) into a gelled emulsion, said formulation comprising:

a. about 0.2 parts by weight of grandlure synthetic boll weevil pheromone,
b. about 5 parts by weight of crude cottonseed oil,
c. about 5 parts by weight of glycerol,
d. about 3.5 parts by weight of organic thickener,
e. about 0.25 parts by weight of a preservative,
f. about 81.25 parts by weight of water, and
g. about 5 parts by weight of an emulsifying agent.

Example 1

A formulation was prepared by mixing grandlure with the following thickened emulsion:

|  | % by weight |
|---|---|
| Crude cottonseed oil (thickened with 6% pyrogenic silica) | 5.00 |
| Glycerol | 5.00 |
| Dacagin (a commercial preparation of locust bean gum) | 1.50 |
| Hydroxyethyl cellulose | 2.00 |
| Sodium benzoate | 0.25 |
| Water | 81.25 |
| Emulsifying Agent (mixture of polyoxyethylene sorbitanmonooleate and sorbitan monooleate) | 5.00 |

Grandlure was added during preparation at the rate of 3 mg per 10 g of emulsion. To prepare, grandlure was mixed with the water, after which the oil and water were emulsified. The other ingredients were then added and mixed. The result was a gelled emulsion, which was poured into ½ oz. plastic jelly cups or coffee creamer cups. Final viscosity was achieved after a few hours in the cups. The cups were covered with aluminum foil or foil-backed paper. To use, the cover was partially peeled back to expose the gel, after which the cup was placed on or in a boll weevil trap.

Example 2

The formula of Example 1 was prepared except that the concentration of oil was increased by 20% with a concurrent decrease in the amount of water.

Example 3

A gel was prepared using the method of Example 1 except that the gel formula consisted of the following:

|  | % by weight |
|---|---|
| polyacrylic acid | 0.50 |
| glyercol | 5.00 |
| 10% NaOH | 2.00 |
| water | 87.50 |

The formulations in the above examples were tested in the field in May 1972. Table 1 below gives the total number of boll weevils captured after 10 days.

TABLE 1

|  | No. of boll weevils captured in field traps after 10 days |
|---|---|
| Formulation in Example 1 | 274 |
| Formulation in Example 2 | 353 |
| Formulation in Example 3 | 128 |

TABLE 1-continued

| | No. of boll weevils captured in field traps after 10 days |
|---|---|
| Empty trap control | 24 |

The formulation of Example 2 was further evaluated in a test designed to compare it with the standard formulation in use (Hardee et al. 1972). Results of this test are below:

| | No. boll weevls captured after 9 days |
|---|---|
| Formulation of Example 2 | 159 |
| Standard formulation | 84 |

This formulation (Example 2) has been used extensively and successfully in survey work. Approximately 130,000 units have been produced and used to date.

I claim:

1. An improved species-specific composition for attracting the boll weevil, *Anthonomus grandis* Boheman, the improvement comprising adding a synthetic boll weevil attractant (grandlure) to a gelled emulsion to prolong activity in the field, said composition containing:
   a. 0.2 parts by weight of grandlure synthetic boll weevil pheromone,
   b. about from 5 to 20 parts by weight of crude cottonseed oil thickened with 6% by weight of pyrogenic silica,
   c. about 5 parts by weight of glycerol,
   d. about 3.5 parts by weight of cellulose and polysaccharide gum type organic thickener selected from the group consisting of hydroxy ethyl cellulose and locust bean gum,
   e. about 0.25 parts by weight of a preservative consisting of equal parts of potassium sorbate and the methyl ester of parahydroxybenzoic acid,
   f. about 5 parts by weight of an emulsifying agent consisting of a mixture of polyoxyethylene sorbitan monooleate and sorbitan monooleate, and
   g. sufficient water to give a total of 100 parts by weight.

* * * * *